United States Patent [19]

Luderer et al.

[11] 4,190,535
[45] Feb. 26, 1980

[54] MEANS FOR SEPARATING LYMPHOCYTES AND MONOCYTES FROM ANTICOAGULATED BLOOD

[75] Inventors: Albert A. Luderer, Corning; Gerald Odstrchel, Horseheads; Anthony R. Zine, Jr., Corning, all of N.Y.

[73] Assignee: Corning Glass Works, Corning, N.Y.

[21] Appl. No.: 922,825

[22] Filed: Jul. 10, 1978

Related U.S. Application Data

[63] Continuation-in-part of Ser. No. 881,252, Feb. 27, 1978, abandoned.

[51] Int. Cl.² ............................................. B01D 21/26
[52] U.S. Cl. ............................ 210/83; 210/DIG. 23
[58] Field of Search ............. 23/230 B; 128/2 F, 2 G, 128/DIG. 5; 210/83, 84, 205, 207, 516, 518, DIG. 23, DIG. 24; 233/1 R, 1 A, 26

[56] References Cited

U.S. PATENT DOCUMENTS

| 3,780,935 | 12/1973 | Lukacs et al. | 210/DIG. 23 |
|---|---|---|---|
| 3,852,194 | 12/1974 | Zine | 233/1 A |
| 3,920,549 | 11/1975 | Gigliello et al. | 210/DIG. 23 |
| 3,957,654 | 5/1976 | Ayres | 233/26 |
| 3,963,119 | 6/1976 | Lukacs et al. | 233/26 |
| 4,021,340 | 5/1977 | Zine | 210/DIG. 23 |
| 4,027,660 | 6/1977 | Wardlaw et al. | 128/DIG. 5 |
| 4,049,692 | 9/1977 | Zine | 233/1 A |
| 4,082,085 | 4/1978 | Wardlaw et al. | 233/1 R |
| 4,083,784 | 4/1978 | Zine | 23/230 B |
| 4,083,788 | 4/1978 | Ferrara | 128/2 G |

FOREIGN PATENT DOCUMENTS 2545749  5/1976  Fed. Rep. of Germany ... 210/DIG. 23

OTHER PUBLICATIONS

Zucker et al., "The Separation of Normal Human Leukocytes by Density and Classification by Size", *Blood*, vol. 34, No. 5, pp. 591–600, (1969).

*Primary Examiner*—Charles N. Hart
*Assistant Examiner*—Ivars Cintins
*Attorney, Agent, or Firm*—William E. Maycock; Clinton S. Janes, Jr.

[57] ABSTRACT

This invention relates to a method for isolating platelets, lymphocytes, and monocytes from anticoagulated blood. The method involves centrifuging at high force a sample of uncoagulated blood with a water-insoluble thixotropic gel-like material having a specific gravity between 1.065–1.077 g/cc for a length of time sufficient to cause the gel-like material to form a barrier between the platelets, lymphocytes, monocytes, and plasma fraction of the blood and the heavier blood cells. Thereafter, the plasma is withdrawn and the platelets, lymphocytes, and monocytes removed from above the barrier in a buffer solution. Where desired, the platelets can be separated from the lymphocytes and monocytes utilizing a similar process but wherein the water-insoluble thixotropic gel-like material has a specific gravity of less than about 1.055 g/cc.

29 Claims, 6 Drawing Figures

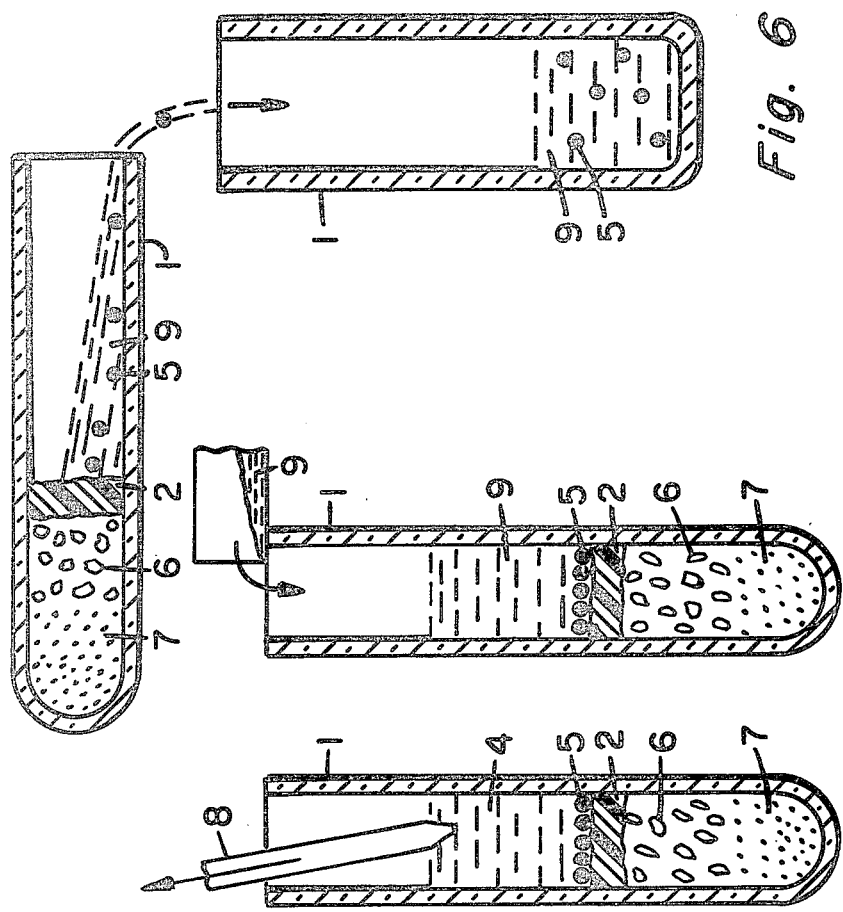

MEANS FOR SEPARATING LYMPHOCYTES AND MONOCYTES FROM ANTICOAGULATED BLOOD

This application is a continuation-in-part of our co-pending application Ser. No. 881,252, filed Feb. 27, 1978, now abandoned.

BACKGROUND OF THE INVENTION

The isolation or separation of white blood cells and, especially, lymphocytes from human blood is clinically necessary for histocompatability determinations, particularly in those instances of patients requiring organ transplants. Determinations of lymphocyte function are indicated where the type and level of medication needed for immunosuppression are at issue.

The present method for isolating lymphocytes and monocytes from anticoagulated human blood drawn by conventional phlebotomy techniques involves bouyant density centrifugation of cells through a particular newtonian fluid, customarily Ficoll-Paque ®, a liquid having a specific gravity of 1.077 g/cc and being marketed by Pharmacia Fine Chemicals AB, Uppsala, Sweden. The method contemplates the following four general steps:

(1) a predetermined amount of Ficoll-Paque ® is dispensed into the bottom of a test tube;

(2) a sample of whole or diluted blood is carefully pipetted onto the Ficoll-Paque ®;

(3) the Ficoll-Paque ®-blood preparation is then centrifuged at about 400–500 G's for about 30–40 minutes such that the blood constituents having a specific gravity greater than the Ficoll-Paque ® (1.077) pass into and/or through that liquid; and, thereafter, (4) the white cells (predominantly lymphocytes) are pipetted off the Ficoll-Paque ® phase.

This method has several disadvantages:

First, if, during the initial pipetting, white cells are accidentally deployed below the surface of the Ficoll-Paque ® medium, the reduced specific gravity of the "local" Ficoll-Paque ® is inadequate to separate the lymphocytes and monocytes.

Second, if, during centrifugation, lighter phases in the blood are carried into the Ficoll-Paque ® medium, they cannot ascend therethrough because of the low buoyant force produced by the 400–500 G's.

Third, centrifugation forces greater than about 400–500 G's cannot be utilized inasmuch as Ficoll-Paque ® is water soluble and greater centrifugation speeds increase the solubility thereof in blood, thereby resulting in a change in its specific gravity.

Fourth, after the centrifugation is completed, the pipetting of the white cells off the Ficoll-Paque ® medium must be undertaken with substantial care because of the newtonian character of the medium.

Fifth, the method requires one-to-two hours for completion—a more rapid process would be highly desirable.

The determination of platelet counts in human blood samples is very important clinically for determining deficiencies in blood clotting. The separation of the platelets from the other blood constituents, particularly the erythrocytes and leucocytes, would make such counting much more rapid. Moreover, in certain types of hemophilia the lack of platelets leads to severe bleeding. One of the procedures which has been devised to counteract this problem has been to administer platelet-enriched plasma at the site of the bleeding to aid in clotting.

The present method for isolating platelets involves drawing blood into an anticoagulated tube and then subjecting to centrifugation. Most of the erythrocytes and leucocytes settle to the bottom of the tube leaving plasma with suspended platelets in the upper layer. The platelet-containing plasma is thereafter carefully pipetted off in an attempt to avoid contamination from the red cells.

As is apparent, the method requires the very tedious step of carefully pipetting off the plasma fraction but, even more importantly, by its very nature the separation of platelets from the red and white cells is not nearly complete.

In certain clinical determinations the presence of platelets obscures the function of lymphocytes and/or monocytes such that their essentially complete separation from the latter two types of cells becomes vital.

SUMMARY OF THE INVENTION

The instant invention is directed to a method for separating lymphocytes and monocytes and, concomitantly, platelets from anticoagulated blood which is much more rapid than the above-described process utilizing Ficoll-Paque ®. Zucker and Cassen, Blood, 34:591, 1969, have demonstrated that lymphocytes possess a lower specific gravity than erythrocytes and granulocytes. Monocytes have a specific gravity closely approximating that of lymphocytes and are present in blood in amounts no more than about 25% of the lymphocyte count. (Platelets have a specific gravity of about 1.025–1.03 g/cc.)

|  | Erythrocytes | Granulocytes | Lymphocytes |
|---|---|---|---|
| Mean Density Distribution Means | 1.0793 g/cc | 1.0747 g/cc | 1.0632 g/cc |
| Standard Deviation | 0.0031 | 0.0054 | 0.0025 |

In its broadest terms, the inventive method contemplates three general steps:

(1) a water-insoluble thixotropic gel-like substance or grease which is chemically inert to blood constituents and having a specific gravity greater than blood platelets, lymphocytes, and monocytes, but less than other cellular elements of blood, is placed in a sample of blood;

(2) the gel-blood sample is centrifuged at high relative centrifugal force, i.e., at a force of at least 1200 G's and, preferably, in excess of 1400 G's during which time the gel-like material will form a barrier between the heavier and lighter blood cells; and (3) the plasma fraction of the blood and the platelets, lymphocytes, and monocytes, which in the separation process pass upward through the gel-like substance, are removed. A count of the cells can then be made.

In the preferred embodiment of the inventive method, the platelets, lymphocytes, and monocytes are separated from the plasma fraction of the blood. This is accomplished via the following steps after the gel-blood sample has been centrifuged and the gel-like material has formed a barrier between the heavier and light portions of the blood;

(a) the plasma fraction of the blood is removed in a manner designed to leave the platelets, lymphocytes, and monocytes intact on the barrier;

(b) a buffer solution compatible with the lighter blood cells, inert to the gel-like material, and having a specific gravity less than that of the gel is deposited upon the gel to provide a suspension medium for the platelets, lymphocytes, and monocytes; and then (c) the suspension of platelets, lymphocytes, and monocytes in buffer solution is removed from contact with the gel.

The formulation or composition of the gel-like substance or grease is not a vital factor so long as the following criteria therefor are met:

(a) the substance should have a specific gravity between about 1.065 and 1.077 g/cc;

(b) the substance must be chemically inert with respect to constituents present in blood;

(c) the substance will be thixotropic, i.e., it will have a thixotropic index greater than 1 and up to 10, in order to minimize the penetration of platelets, lymphocytes, and monocytes into the barrier following centrifugation; and (d) the substance should exhibit sufficient viscosity, when subjected to centrifugal forces of at least about 1200 G's and efficaciously up to 2500 G's, to flow and thereby form the desired barrier between the platelets, lymphocytes, and monocytes and the heavier blood cells.

The inventive method is operable with both the conventional opened and closed blood collection tubes. In the opened collection tube system, the gel-like material will customarily be inserted into the tube immediately prior to the centrifugation operation. Frequently, the gel will be placed on the inner wall of the tube at a position above the blood sample level. In the closed collection tube system, the gel-like material can be placed anywhere within the tube prior to closing the tube via a rubber stopper or other conventional means. In general, glass or plastic collection tubes will be employed.

Where a separation of the platelets from the lymphocytes and monocytes is desired, the plasma fraction of the blood containing the platelets, lymphocytes, and monocytes can be subjected to the same general inventive method steps but the water-insoluble thixotropic gel-like substance or grease will be utilized having a specific gravity of less than 1.055 g/cc, generally between 1.03–1.055 g/cc. It will be apparent, of course, that where a simple separation of platelets from the total spectrum of red and white cells is desired, the inventive method can be employing a barrier gel-like material having a specific gravity of less than 1.055 g/cc.

BRIEF DESCRIPTION OF THE DRAWINGS

FIGS. 1–6 depict the preferred embodiment of the inventive method.

FIG. 1 represents an opened blood collection tube containing a sample of whole blood and gel-like substance;

FIG. 2 illustrates the gel-blood sample mixture during the centrifugation process, the gel having moved from its original position into the blood sample.

FIG. 3 depicts the state of the gel-blood sample mixture upon reaching equilibrium during centrifugation, the gel having flowed to form a barrier between the platelets, lymphocytes, monocytes, and plasma fractions of the blood and the heavier portions thereof.

FIG. 4 discloses removing the plasma fraction.

FIG. 5 shows the addition of buffer solution.

FIG. 6 illustrates decanting off the suspension of lymphocytes in buffer solution.

PRIOR ART

U.S. Pat. No. 3,852,194 discloses means for separating heavier phases present in blood samples from lighter phases therein utilizing a thixotropic gel-like material having a specific gravity intermediate of the phases to be separated. The gel is centrifuged along with the blood sample and, during that operation, the gel flows to provide a barrier between the phase to be separated. The barrier permits easy and substantially complete removal of the phase resting thereupon.

The patent notes the use of a wide variety of gel-like materials or greases for the process. Three criteria are cited as being mandatory attributes of those materials.

(1) a specific gravity intermediate the phases sought to be separated, noting utility of materials having specific gravities between 1.035–1.06 g/cc and, preferably, between 1.04–1.055 g/cc;

(2) no chemical reaction with the phases sought to be separated; and (3) essentially non-flowable (semi-rigid) when at rest.

The patent has no disclosure relating to the isolation of lymphocytes and monocytes or to a process involving centrifugation forces of at least 1200 G's and, preferably, in excess of 1400 G's. Such high forces are demanded to effect a sufficiently high resulting buoyant force to cause the lymphocytes and monocytes to rise to the gel-plasma interface.

U.S. Pat. No. 3,920,549 sets forth a modification of and an improvement upon the invention of U.S. Pat. No. 3,852,194, supra. The improvement upon the earlier disclosure involved the use of solid element inserted into the blood collection tube, denominated an "energizer," having a specific gravity greater than that of the gel. During the centrifugation operation, the energizer impacts upon the gel (normally placed in the bottom of the blood collection tube) thereby facilitating movement of the gel upwards along the walls of the tube. The inclusion of the energizer expedites the separation of the blood fractions and provides a cleaner separation therebetween.

Whereas the patent mentions the use of relatively high centrifugation forces (1100 G's), there is no discussion of separating lymphocytes and monocytes from the other components of blood and the specific gravity of the gel-like materials used again ranged between 1.035 and 1.06 g/cc, with 1.04–1.055 g/cc being preferred.

U.S. Pat. No. 3,963,119 describes a dispensing device for depositing a sealant material into a blood collection tube, the sealant material being of the same type and performing the same function as the gel-like substances described in U.S. Pat. Nos. 3,852,194 and 3,920,549, supra.

Whereas the patent speaks of sealants having specific gravities between 1.026–1.092 g/cc, the preferred range is stated to be 1.030–1.050 g/cc. There is no discussion regarding the isolation of lymphocytes and monocytes from other constituents of blood, nor any indication of the utility of high centrifugal forces, i.e., at least 1200 G's.

DESCRIPTION OF PREFERRED EMBODIMENTS

In the following examples which illustrate the preferred embodiment of the inventive method, the gel-like material or grease employed consisted of a mixture of silicone fluid and very fine hydrophobic silica powder. The silicone fluid used was Dow Corning 200 Fluid, a dimethyl polysiloxane liquid manufactured by Dow Corning Corporation, Midland, Mich. and described in Dow Corning Bulletins CPO-1072, March, 1972 and CPO-158-1, March, 1972. Silanox® 101, manufactured by the Cabot Corporation, Boston, Mass., and described in Cabot brochure SGEN-1, was utilized as the powdered silica material. The material is fumed silica having trimethyl groups bonded to the surface thereof to impart hydrophobic character. Nevertheless, as was explained above, non-silicone thixotropic gel-like substances can be utilized with equal facility so long as the necessary property criteria are met.

Whole human blood was drawn and placed into 7 ml glass collection tubes containing sufficient EDTA to act as an anticoagulant. About 1.5 ml of a silicone fluid-hydrophobic silica powder gel-like mass was deposited onto the inner wall of the tube above the blood sample.

FIG. 1 is illustrative of the collection tube containing the blood sample. Thus, gel-like mass 2 was deposited onto the inner wall of an open-ended tube 1 at the upper end thereof after blood sample 3 had been collected.

The blood sample was centrifuged at about 1800 G's until equilibrium was reached, this customarily requiring about 5–10 minutes. FIG. 2 represents the gel-blood mixture during the centrifugation step but before equilibrium has been reached. The gel-like mass 2 has moved down tube 1 and the heavier and ligher components of the blood sample 3 have begun to separate from each other. FIG. 3 portrays the situation when centrifugation has been carried out equilibrium. As can be seen, the gel-like mass 2 has separated the lighter and heavier components of the blood sample from each other. Thus, the plasma fraction of the blood 4 and the platelets, lymphocytes, and monocytes 5 ride upon barrier mass 2, whereas the granulocytes 6 and red blood cells 7 (with other heavier portions of the blood) are retained below barrier 2.

The plasma factor 4 of the blood was then removed, care being exercised to avoid disturbing platelets, lymphocytes, and monocytes 5. FIG. 4 exhibits carrying out that operation by means of a pipette 8, leaving the platelets, lymphocytes, and monocytes 5 on barrier 2.

Thereafter (FIG. 5), an isotonic $Ca^{+2}$,$Mg^{+2}$-free salt buffer solution 9 was gently run into tube 1 onto gel barrier 2.

Subsequently, tube 1 was gently rocked or otherwise agitated to cause the platelets, lymphocytes, and monocytes 5 which had been resting on gel barrier 2 to be suspended in buffer solution 9, and this suspension then removed from tube 1. FIG. 6 illustrates this removal being performed by decanting the suspension off of gel barrier 2.

As with other methods for separating platelets, lymphocytes, and monocytes, the recovered cells were washed with buffer solutions and counted cells could thereafter be utilized in various bioassays.

Results from three silicone fluid-powdered $SiO_2$ mixtures of different specific gravities and thixotropic indices are reported in the table below.

| Gel | Specific Gravity | Thixotropic Index | % of Total Cells in Unfractionated Blood | | % of Total Recovered Cells in Gel Fractionated Blood | cation cation Factor | % Viable |
|---|---|---|---|---|---|---|---|
| 1 | 1.0678 | 4.44 | N | 74 | 23 | −3.2 | 100% |
|   |        |      | L | 20 | 72 | +3.6 |      |
|   |        |      | M | 5  | 5  | +1.0 |      |
|   |        |      | E | 1  |    |      |      |
|   |        |      | B | 0  |    |      |      |
| 2 | 1.0677 | 2.07 | N | 74 | 13 | −5.7 | 96%  |
|   |        |      | L | 20 | 80 | +4.0 |      |
|   |        |      | M | 5  | 7  | +1.4 |      |
|   |        |      | E | 1  |    |      |      |
|   |        |      | B | 0  |    |      |      |
| 3 | 1.0674 | 1.32 | N | 74 | 28 | −2.6 | 95%  |
|   |        |      | L | 20 | 61 | +3.05 |     |
|   |        |      | M | 5  | 10 | +2.0 |      |
|   |        |      | E | 1  | 1  |      |      |
|   |        |      | B | 0  |    |      |      |

N = Neutrophil
L = Lymphocyte
M = Monocyte
E = Eosinophil B = Basophil
Purification Factor: + equals enrichment and − equals depletion based upon unfractionated blood
Normal viability in Ficoll-Paque® separations averages between 90–100%

The validity of the postulated cell distribution represented in FIG. 3 is confirmed by the above data. In each case lymphocytes were highly enriched whereas neutrophils (the principal granulocyte) were greatly reduced when compared with the original whole blood sample. The proportion of monocytes was also increased, but to a somewhat lesser extent. Cell viability, as determined by trypan blue dye exclusion, was $\geq 95\%$. Such data clearly indicate the feasibility of this method for the isolation of lymphocytes from blood samples.

Although the above laboratory work was undertaken with opened blood collection tubes, it will be recognized that a closed system can be equally operative. In such a system, the blood sample will be drawn into a collection tube containing the thixotropic gel-like material and a sufficient amount of a substance, such as EDTA, to inhibit coagulation. The drawn sample is thereafter centrifuged, the plasma withdrawn, and the lymphocytes and monocytes then recovered.

As was observed above, non-silicone thixotropic gel-like substances can be used. For example, a hydrocarbon gel-like material polybutene H-100, marketed by Amoco Chemicals Corporation, Chicago, Ill., and described in that company's bulletin 12-H as a butylene polymer composed predominantly of high molecular weight mono-olefins (85–98%), the balance being isoparaffins, when mixed with AEROSIL OX50, a fumed silica powder marketed by Degussa, Inc., Pigments Division, New York, N.Y., will perform in like manner to the above-described silicone material. With the hydrocarbon polymer it is not necessary to render the filler material hydrophobic.

A mixture of 100 grams of the polybutene H-100 and 39.42 grams of the OX50 silica filler exhibited a specific gravity of 1.0672 g/cc and a thixotropic index of 2.77.

Another example of a useful hydrocarbon gel-like material is Poly bd ® R-45HT, marketed by ARCO Chemical Company, New York, N.Y. and described in that company's general bulletin of April, 1976 as a hydroxyl terminated homopolymer of butadiene with the degree of polymerization being in the range of 50. Again, a non-hydrophobic filler material can be used with this polymer.

A mixture composed of 100 grams of that material with 34.33 grams of the OX50 silica filler demonstrated a specific gravity of 1.0675 g/cc and a thixotropic index of 1.25.

These hydrocarbon polymer-silica mixtures meet the above-demanded criteria for the present invention. That is:

(a) they have a specific gravity between about 1.065–1.077 g/cc;
(b) they are chemically inert to blood constituents;
(c) they have a thixotropic index greater than 1 and up to 10; and
(d) they exhibit sufficient viscosity such that at centrifugal forces up to 2500 G's they will flow and form the desired barrier between the platelets, lymphocytes, and monocytes and the heavier blood cells.

U.S. Pat. No. 3,852,194, supra, recites several gel-like materials having specific gravities of less than 1.055 g/cc which would be effective in the present invention for separating platelets from lymphocytes and monocytes (and from other red cells and white cells of the blood). The substances reported there consisted of mixtures of silicone fluids and hydrophobic powdered silica. It will be appreciated, of course, that hydrocarbon polymer-silica gel-like mixtures can also be formulated which demonstrate the required specific gravity.

To illustrate the general effectiveness of the inventive method for separating platelets, whole human blood was drawn and placed into a 7 ml glass collection tube containing sufficient EDTA to prevent coagulation of the blood. About 1.5 ml of a silicone fluid-hydrophobic silica powder gel-like mass having a specific gravity of 1.040 g/cc was deposited upon the inner wall of the tube above the blood sample. The blood sample was centrifuged at about 1200 G's for above five minutes, the gel-like mass forming a barrier separating the platelet-containing plasma and the red and white cells. The plasma factor of the blood containing the platelets was pipetted off the barrier gel.

Slides were prepared using whole blood and the platelet-containing plasma. The platelet count on both slides was about 200,000 and microscopic examination of the plasma indicated the essential absence of contamination with red and white cells.

We claim:

1. A method for separating platelets, lymphocytes, and monocytes from anticoagulant blood comprising the steps:
    (a) a water-insoluble thixotropic gel-like substance which is chemically inert to blood constituents and having a specific gravity between 1.065–1.077 g/cc is placed in a sample of anticoagulated blood;
    (b) the gel-blood sample is centrifuged at a force of at least 1200 G's for a sufficient length of time to cause the gel-like substance to form a barrier between the plasma, platelets, lymphocytes, and monocytes and the heavier blood cells; and, thereafter,
    (c) the plasma, platelets, lymphocytes, and monocytes are removed from atop said barrier.

2. A method according to claim 1 wherein said gel-like substance consists of a mixture of silicone fluid and a hydrophobic powdered silica.

3. A method according to claim 1 wherein said gel-like substance consists of a mixture of hydrocarbon polymer and a powdered silica.

4. A method according to claim 3 wherein said hydrocarbon polymer is selected from the group of a butylene polymer composed predominantly of high molecular weight mono-olefins with the balance being isoparaffins, and a hydroxyl terminated hompolymer butadiene with the degree of polymerization being about 50.

5. A method according to claim 1 wherein said gel-like substance has a thixotropic index greater than 1 and up to 10.

6. A method according to claim 1 wherein said centrifugation is conducted at a force between 1200–2500 G's.

7. A method according to claim 1 wherein said centrifugation is conducted for a period of about 5–10 minutes.

8. A method for separating platelets, lymphocytes, and monocytes from anticoagulant blood comprising the steps:
    (a) a water-insoluble thixotropic gel-like substance which is chemically inert to blood constituents and having a specific gravity between 1.065–1.077 g/cc is placed in a sample of anticoagulated blood;
    (b) the gel-blood sample is centrifuged at a force of at least 1200 G's for a sufficient length of time to cause the gel-like substance to form a barrier between the plasma, platelets, lymphocytes and monocytes and the heavier blood cells;
    (c) the plasma is removed from atop said barrier leaving said platelets, lymphocytes and monocytes resting thereupon;
    (d) a buffer solution compatible with platelets, lymphocytes, and monocytes, inert to the gel-like substance, and having a specific gravity less than that of the gel-like substance is deposited upon said barrier;
    (e) the buffer solution is agitated to cause the said platelets, lymphocytes, and monocytes to become suspended therein; and then
    (f) the suspension of platelets, lymphocytes, and monocytes in buffer is removed from contact with said barrier.

9. A method according to claim 8 wherein said gel-like substance consists of a mixture of silicone fluid and a hydrophobic powdered silica.

10. A method according to claim 8 wherein said gel-like substance consists of a mixture of hydrocarbon polymer and a powdered silica.

11. A method according to claim 10 wherein said hydrocarbon polymer is selected from the group of a butylene polymer composed predominantly of high molecular weight mono-olefins with the balance being isoparaffins, and a hydroxyl terminated homopolymer of butadiene with the degree of polymerization being about 50.

12. A method according to claim 8 wherein said gel-like substance has a thixotropic index greater than 1 and up to 10.

13. A method according to claim 8 wherein said centrifugation is conducted at a force between 1200–2500 G's.

14. A method according to claim 8 wherein said centrifugation is conducted for a period of about 5–10 minutes.

15. A method according to claim 8 wherein said buffer solution is an isotonic $Ca^{+2},Mg^{+2}$-free salt solution.

16. A method for separating platelets from lymphocytes and monocytes comprising the steps:
   (a) a water-insoluble thixotropic gel-like substance which is chemically inert to blood constituents and having a specific gravity between 1.03–1.055 g/cc is placed in a blood plasma sample of anticoagulated blood containing platelets, lymphocytes, and monocytes;
   (b) the gel-plasma sample is centrifuged at a force of at least 1200 G's for a sufficient length of time to cause the gel-like substance to form a barrier between the plasma and platelets and the lymphocytes and monocytes; and, thereafter,
   (c) the plasma and platelets are removed from atop said barrier.

17. A method according to claim 16 wherein said gel-like substance consists of a mixture of silicone fluid and a hydrophobic powdered silica.

18. A method according to claim 16 wherein said gel-like substance consists of a mixture of hydrocarbon polymer and a powdered silica.

19. A method according to claim 18 wherein said hydrocarbon polymer is selected from the group of a butylene polymer composed predominantly of high molecular weight mono-olefins with the balance being isoparaffins, and a hydroxyl terminated homopolymer butadiene with the degree of polymerization being about 50.

20. A method according to claim 16 wherein said gel-like substance has a thixotropic index greater than 1 and up to 10.

21. A method according to claim 16 wherein said centrifugation is conducted at a force between 1200–2500 G's.

22. A method according to claim 16 wherein said centrifugation is conducted for a period of about 5–10 minutes.

23. A method for separating platelets from anticoagulant blood comprising the steps:
   (a) a water-insoluble thixotropic gel-like substance which is chemically inert to blood constituents and having a specific gravity between 1.03–1.055 g/cc is placed in a sample of anticoagulated blood;
   (b) the gel-blood sample is centrifuged at a force of at least 1200 G's for a sufficient length of time to cause the gel-like substance to form a barrier between the plasma and platelets and the heavier blood cells; and, thereafter,
   (c) the plasma and platelets are removed from atop said barrier.

24. A method according to claim 23 wherein said gel-like substance consists of a mixture of silicone fluid and a hydrophobic powdered silica.

25. A method according to claim 23 wherein said gel-like substance consists of a mixture of hydrocarbon polymer and a powdered silica.

26. A method according to claim 25 wherein said hydrocarbon polymer is selected from the group of a butylene polymer composed predominantly of high molecular weight mono-olefins with the balance being isoparaffins, and a hydroxyl terminated homopolymer butadiene with the degree of polymerization being about 50.

27. A method according to claim 23 wherein said gel-like substance has a thixotropic index greater than 1 and up to 10.

28. A method according to claim 23 wherein said centrifugation is conducted at a force between 1200–2500 G's.

29. A method according to claim 23 wherein said centrifugation is conducted for a period of about 5–10 minutes.

* * * * *

UNITED STATES PATENT AND TRADEMARK OFFICE
CERTIFICATE OF CORRECTION

PATENT NO. : 4,190,535
DATED : February 26, 1980
INVENTOR(S) : Albert A. Luderer, Gerald Odstrchel, Anthony R. Zine, Jr.

It is certified that error appears in the above-identified patent and that said Letters Patent are hereby corrected as shown below:

Column 5, line 56, change "out" to -- to --.

Column 6, line 3 of the table, change "cation" to -- Purifi --.

Column 6, line 24 of the table, delete "B = Basophil" and add as a new line directly under "E = Eosinophil", -- B = Basophil --.

Signed and Sealed this

Twenty-fourth Day of June 1980

[SEAL]

Attest:

SIDNEY A. DIAMOND

Attesting Officer

Commissioner of Patents and Trademarks